United States Patent [19]

Sarnoff

[11] Patent Number: 4,656,034

[45] Date of Patent: Apr. 7, 1987

[54] ABSORPTION ENHANCING AGENTS

[75] Inventor: Stanley J. Sarnoff, Bethesda, Md.

[73] Assignee: Survival Technology, Inc., Bethesda, Md.

[21] Appl. No.: 735,734

[22] Filed: May 20, 1985

[51] Int. Cl.$^4$ ............................................. A61K 37/50
[52] U.S. Cl. .................................... 424/94; 424/127; 514/2; 514/114; 514/257; 514/264; 514/425; 514/588; 514/614; 514/632; 514/634; 514/645
[58] Field of Search ...................... 424/94, 127; 514/2, 514/114, 257, 264, 588, 634, 614, 645, 425, 632

[56] References Cited
U.S. PATENT DOCUMENTS 3,629,410 12/1971 Heiffer et al. ........................ 514/114
4,292,311 9/1981 Sarnoff ................................. 424/10

OTHER PUBLICATIONS

Mil'chakov et al.–Chem. Abst. vol. 98 (1983) p. 46932g.
Lankin et al.–Chem. Abst. vol. 97 (1982) p. 21610s.

Primary Examiner—Sam Rosen
Attorney, Agent, or Firm—Cushman, Darby & Cushman

[57] ABSTRACT

The absorption of a scavenger of oxygen free radicals generated at the time of reperfusion or the absorption of an agent preventing the cytotoxic effects on healthy cells in a mammal. e.g. superoxide dismutase or S-aminotrimethyleneaminoethyl thiophosphate is enhanced by substantially simultaneously administering an absorption enhancing agent therefore, e.g. hydroxylamine or a non-toxic salt thereof. It is also part of the invention to inject WR-2721 intravenously or intramuscularly as a scavenger of oxygen free radicals even in the absence of an absorption enhancing agent.

67 Claims, No Drawings

ABSORPTION ENHANCING AGENTS

BACKGROUND OF THE INVENTION

Reference is made to Sarnoff application 638,695, filed Aug. 8, 1984 and Sarnoff application 708,845, filed Mar. 6, 1985 which disclose the use of a t-PA absorption enhancing agent, e.g. hydroxylamine or a non-toxic salt thereof, preferably hydroxylamine hydrochloride, to increase the absorption of t-PA in the blood when the t-PA is administered intramuscularly. The entire disclosures of both prior Sarnoff applications is hereby incorporated by reference and relied upon.

Superoxide dismutase (SOD) is a protein, specifically an enyzme, which has been used to ameliorate the side effects of radiation therapy, more especially to protect the healthy cells.

Superoxide dismutase has also been employed to scavenge oxygen free radicals generated at the time of reperfusion and thus to diminish myocardium damage. Oxygen derived free radicals include the superoxide radical $O_2-$ and the more reactive hydroxyl radical OH which may be produced secondarily from superoxide.

In the JACC Volume 5, No. 2, February 1985 there are Abstracts of a number of articles on this subject. Thus there is an Abstract of an article by Ambrosio et al entitled "Reduction In Reperfusion Injury With Recombinant Human Superoxide Dismutase Following Global Ischemia" on page 489 and also on page 489 an Abstract of an article by Werns et al entitled "Superoxide Dismutase But Not Catalase Protects Reperfused Ischemic Myocardium." Also there is an Abstract of an article by Horneffer et al entitled "Reperfusion Injury Prevented By Oxygen Free Radical Scavenger: Functional and Morphological Evidence" one page 541 and an Abstract of an article by Myers et al entitled "Superoxide Dismutase And Catalase Enhance Recovery Of Myocardial Function Following Reversible Ischemia on page 542. The entire disclosure of these four articles is hereby incorporated by reference and relied upon. The Horneffer et al article points out that with reperfusion of ischemic myocardium, there is production of cytotoxic oxygen free-radicals. Horneffer et al tested SOD to see whether it might improve the salvage of ischemic myocardium. It was found that infusion of SOD in pigs after reversible coronary occlusion prevented reperfusion injury and improved myocardial salvage. Similar results were obtained by Meyers et al on dogs using 5 mg/kg (3100 U/mg) of SOD. Ambrosio et al found that recombinant human superoxide dismutase (SOD) reduced reperfusion injury.

Recently McCord, the New England Journal of Medicine Volume 312 No. 3, pages 159–163 (the entire disclosure of which is hereby incorporated reference and relied upon), pointed out that "ischemic injury" in many cases is a misnomer and that a substantial part of the injury may be more properly called reperfusion injury and occurs during the period when molecular oxygen is reintroduced into the tissue. It was also noted by McCord that the primary source of superoxide in reperfused reoxygenated tissues appears to be the enzyme xanthine oxidase released during ischemia by a calcium-triggered proteolytic attack on xanthine dehydrogenase. Reperfused tissues can be protected by scavengers of superoxide radicals or hydroxyl radials or by allopurinol or other inhibitors of xanthine oxidase, e.g. alloxanthine.

The compound WR-2721 [$H_2N(CH_2)_3NHCH_2CH_2SPO_3H_2$] has been used to protect against the cytotoxic effects of irradiation. WR-2721 also protects the healthy cells when treating cancer with chemotherapy.

It has now been discovered that WR-2721 can be used in place of SOD to scavenge oxygen free radicals generated at the time of reperfusion. The WR-2721 can be administered either intravenously or intramuscularly in the same manner as SOD and in the same dosage.

Additionally it has now been found there can be obtained more rapid and prolonged reperfusion and thrombolysis by the intramuscular administration of a scavenger of oxygen free radicals or hydroxyl groups, e.g. superoxide dismutase or other proteins, e.g. enzymes which act as scavengers or WR-2721 or analogous materials together with an agent enhancing the absorption of the scavenger. Likewise, there can be administered intramuscularly inhibitors of xanthine oxidase such as allopyrinol and alloxanthine.

Furthermore, the intramuscular administration of SOD or WR-2721 and related materials can be employed when these agents are employed as protective agents for healthy cells in treating cancer by irradiation or chemotherapy.

The intramuscular administration of the present invention is of importance where there is a need for a fast response time and it cannot be obtained by intravenous injection.

In place of WR-2721 there can also be employed analogous materials of the formula $$H_2N-R(NHR_2)_x-NHR_3-SPO_3H_2 \qquad (I)$$

where $R_1$, $R_2$, and $R_3$ are each alkylene of at least two carbon atoms, e.g. 2 to 6 carbon atoms and x is zero or a small integer, e.g. 1 to 3. WR-2721 is the compound within formula I which is S-aminotrimethyleneaminoethyl thiophosphate. Other compounds within this formula are S-aminoethyleneaminoethyl thiophosphate, S-aminoethyleneaminopropyl thiophosphate, S-aminoethyleneaminoethyleneaminoethyl thiophosphate.

The invention includes packaging the scavenger, xanthine oxidase inhibitor or cell protective agent with the agent enhancing the absorption of the scavenger, inhibitor or cell protective agent in the blood. The enhancing agent preferably is hydroxylamine hydrochloride. There can be used for example a known emergency type automatic injector and the process comprises injecting the two medicament agents into the muscle tissue.

In accordance with the principles of the present invention, the absorption rate of SOD, WR-2721 and other scavengers and protective agents in the blood is enhanced by utilizing with the SOD, WR-2721 or other scavenger or protective agent dosage, a dosage of an absorption enhancing agent for SOD, WR-2721 or the like, preferably hydroxylamine hydrochloride. Preferably, the absorption enhancing agent such as hydroxylamine hydrochloride is mixed in with the SOD, WR-2721 or other scavenger or protective agent dosage to form a single mixed dosage which is then injected intramuscularly (i.m.), e.g. as described in the Sarnoff application 638,695. It is within the contemplation of the present invention to inject the absorption enhancing agent as a separate dosage within the same site as the separate dosage of SOD, WR-2721 or other scavenger or protective agent (e.g. U.S. Pat. No. 4,394,863). An example of an amount of absorption enhancing agent, such as hydroxylamine hydrochloride, which is added to the SOD, WR-2721 or other scavenger or protective agent dosage, as previously described, to form a single mixed dosage is an amount of from 0.25 to 100 milligrams per kilogram of body weight. For example with dogs using a dosage of 5 mg/kg of SOD there can be used 5 mg/kg of hydroxylamine hydrochloride.

As the absorption enhancing agent hydroxylamine is preferably employed in the form of a non-toxic water soluble salt. Thus there can be used for example in place of hydroxylamine salts such as hydroxylamine hydrochloride, hydroxylamine hydrobromide, hydroxylamine hydroiodide, hydroxylamine sulfate, hydroxylamine nitrate, hydroxylamine acetate, and hydroxylamine propionate. Most preferably there is employed hydroxylamine hydrochloride.

There is also contemplated as absorption enhancing agents in accordance with the invention compounds such as urea, mono and dialkyl ureas, e.g. methyl urea, ethyl urea, propyl urea, butyl urea, N,N-dimethyl urea, N,N-diethyl urea, N,N-diisopropyl urea, mono and dialkyl ureas, e.g. phenyl urea, p-tolylurea, N,N-diphenyl and urea, N,N-di-p-tolyl urea, thiourea, hydantoin, 5-substituted hydantoins, e.g. 5-alkyl, 5-aralkyl, and 5-aryl hydantoins and 5,5-dialkyl and 5,5-diaryl hydantoins, e.g. 5-methyl hydantoin, 5-ethyl hydantoin, 5,5-dimethyl hydantoin, 1,5-trimethylene hydantoin, 1,5-tetramethylene hydantoin, 5-phenyl hydantoin, 5-p-tolyl-hydantoin, and 5,5-diphenyl hydantoin, guanidine, methyl guanidine, hydrazine, alkyl and aryl hydrazines, e.g. methyl hydrazine, ethyl hydrazine, butyl hydrazine, phenyl hydrazine and diphenyl hydrazine, alkyl and aryl hydroxylamines, e.g. methyl hydroxylamine, ethyl hydroxylamine and phenyl hydroxylamine. The substituted ureas, hydrazines and hydroxylamines likewise can be used in the form of salts, e.g. as hydrochlorides.

The simultaneous administration of SOD, WR-2721 or other scavenger, inhibitor or protective agent and absorption enhancing agent is intended for not only human use but it is within the scope of the invention that they be administered for veterinary purposes, e,g. to other mammals, e.g. dogs, cats, cattle, rabbits, and horses.

While it is not necessary to employ catalase with the SOD there can be simultaneously employed catalase, e.g. to possibly further prolong the activity of SOD as mentioned by Werns et al.

In another aspect the invention includes a method of treating a mammal, e.g. any of those mentioned previously with a liquid medicament under circumstances where intravenous injection is not practical but the fast response time of an intravenous injection is desirable. This is accomplished by administering in liquid form the medicament together with hydroxylamine or a non-toxic salt thereof, e.g. any of those mentioned above intramuscularly. There can be used for example, either a single mixed dosage or separate dosages in the manner set forth above.

The hydroxylamine or salt thereof can be used in an amount of from 0.25 to 100 milligrams per kilogram of body weight. Thus for example, to treat hyperglycemia there an be injected intramuscularly to a 150 pound individual 1-2 mg of glucagon and 350 mg of hydroxylamine hydrochloride.. Also there can be injected intramuscularly to a 150 pound individual in need of lidocaine 300 mg of lidocaine and 350 mg of hydroxylamine hydrochloride. With insulin for example, 21 units of regular insulin can be injected together with 350 mg of hydroxylamine hydrochloride.

The allopurinol or alloxanthine can be administered intramuscularly, e.g. in an amount of 1-1000 mg, e,g. 250 mg, without hydroxylamine or salt thereof. However, to enhance the absorption of the xanthine oxidase inhibitor it is preferred to add the hydroxyl amine or salt thereof. Thus there can be injected intramuscularly 100 mg of allopurine together with 350 mg of hydroxylamine hydrochloride.

What is claimed is:

1. In a method of administering a scavenger of oxygen free radicals generated at the time of reperfusion and diminishing myocardium damage to a mammal, the improvement comprising increasing the absorption of the scavenger in the blood by substantially simultaneously intramuscularly administering the scavenger and an amount of scavenger absorption enhancing agent effective to increase the absorption of the scavenger.

2. A method according to claim 1 wherein the absorption enhancing agent is hydroxylamine or a non-toxic salt thereof.

3. A method according to claim 2 wherein the absorption enhancing agent is hydroxylamine hydrochloride.

4. A method according to claim 1 wherein the mammal is a human.

5. A method according to claim 2 wherein the mammal is a human.

6. A method according to claim 3 wherein the mammal is a human.

7. A method according to claim 4 wherein the scavenger is a protein.

8. A method according to claim 7 wherein the scavenger is an enzyme.

9. A method according to claim 8 wherein the scavenger is superoxide dismutase.

10. A method according to claim 5 wherein the scavenger is superoxide dismutase.

11. A method according to claim 6 wherein the scavenger is superoxide dismutase.

12. A method according to claim 4 wherein the scavenger is an S-aminopolyalkyleneaminoalkyl thiophosphate.

13. A method according to claim 4 wherein the scavenger is S-aminotrimethyleneaminoethyl thiophosphate.

14. A method according to claim 5 wherein the scavenger is S-aminotrimethyleneaminoethyl thiophosphate.

15. A method according to claim 6 wherein the scavenger is S-aminotrimethyleneaminoethyl thiophosphate.

16. In a method of employing an agent for preventing the cytotoxic effects on healthy cells in a mammal which is subjected to irradiation or chemical therapy in the treatment of cancer, the improvement comprising increasing the absorption of the agent for presenting cytotoxic effects in the blood by substantially simultaneously intramuscularly administering said agent and an amount of an absorption enhancer for said agent effective to increase the absorption of said agent.

17. A method according to claim 16 wherein the mammal is a human.

18. A method according to claim 17 wherein the enhancer is hydroxylamine or a non-toxic salt thereof.

19. A method according to claim 18 wherein the agent is superoxide dismutase.

20. A method according to claim 19 wherein the enhancer is hydroxylamine hydrochloride.

21. A method according to claim 18 wherein the agent is S-aminotrimethyleneaminoethyl thiophosphate.

22. A method according to claim 21 wherein the enhancer is hydroxylamine hydrochloride.

23. A package containing (1) (A) a scavenger of oxygen free radicals generated at the time of reperfusion in a mammal or (B) an agent which prevents cytotoxic effects on healthy cells when a mammal is subjected to irradiation or chemotherapy and (2) a substance enhancing the absorption of said scavenger or cytatoxic effect presenting agent in the blood in an amount effective to enhance the absorption of said scavenger or agent when administered intramuscularly.

24. A package according to claim 23 wherein the absorption enhancing substance is hydroxylamine or a non-toxic salt thereof.

25. A package according to claim 24 wherein the absorption enhancing substance is hydroxylamine hydrochloride.

26. A package according to claim 23 wherein (1) and (2) are kept separate prior to use.

27. A package according to claim 26 wherein (2) is hydroxylamine or a non-toxic salt thereof.

28. A package according to claim 26 wherein the absorption enhancing agent is hydroxylamine hydrochloride.

29. A package according to claim 23 wherein (1) is superoxide dismutase.

30. A package according to claim 29 wherein the absorption enhancing substance is hydroxylamine or a non-toxic salt thereof.

31. A package according to claim 30 wherein the absorption enhancing substance is hydroxylamine hydrochloride.

32. A package according to claim 23 wherein (1) is S-aminotrimethyleneaminoethyl thiophosphate.

33. A package according to claim 32 wherein the absorption enhancing substance is hydroxylamine or a non-toxic salt thereof.

34. A package according to claim 33 wherein the absorption enhancing substance is hydroxylamine hydrochloride.

35. A method of scavenging oxygen free radicals generated at the time of reperfusion and diminishing myocardium damage to a mammal comprising administering to the mammal at the time of reperfusion as a scavenger of oxygen free radicals the compound S-aminotrimethyleneaminoethyl thiophosphate in an amount sufficient to scavenge oxygen free radicals.

36. A method according to claim 35 wherein the compound is administered intravenously.

37. A method according to claim 35 wherein the compound is administered intramuscularly.

38. A method according to claim 35 wherein the mammal is a human.

39. A method of treating a mammal with a liquid medicament under circumstances where intravenous injection is not practical but the fast response time of an intravenous injection is desirable, said method comprising administering the medicament intramuscularly substantially simultaneously with hydroxylamine or a non-toxic salt thereof in an amount effective to reduce the response time to the medicament.

40. A method according to claim 39 wherein there is employed hydroxylamine hydrochloride.

41. A method according to claim 39 wherein the medicament is lidocaine.

42. A method according to claim 41 wherein there is employed hydroxylamine hydrochloride.

43. A method according to claim 39 wherein there is administered glucagon.

44. A method according to claim 43 wherein there is employed hydroxylamine hydrochloride.

45. A method according to claim 39 wherein there is administered insulin.

46. A method according to claim 45 wherein there is employed hydroxylamine hydrochloride.

47. In a method of administering an inhibitor xanthine oxidase during reperfusion and diminishing myocardium damage to a mammal, the improvement comprising increasing the absorption of the inhibitor in the blood by substantially simultaneously intramuscularly administering the inhibitor and an amount of inhibitor absorption enhancing agent effective to increase the absorption of the inhibitor.

48. A method according to claim 47 wherein the absorption enhancing agent is hydroxylamine or a non-toxic salt thereof.

49. A method according to claim 48 wherein the absorption enhancing agent is hydroxylamine hydrochlride.

50. A method according to claim 47 wherein the mammal is a human.

51. A method according to claim 48 wherein the mammal is a human.

52. A method according to claim 49 wherein the mammal is a human.

53. A method according to claim 50 wherein the inhibitor is allopurine.

54. A method according to claim 53 wherein the inhibitor is alloxanthine inhibitor.

55. A package containing (1) an inhibitor of xanthine oxidase and (2) a substance enhancing the absorption of said inhibitor in the blood in an amount effective to enhance the absorption of said inhibitor when administered intramuscularly.

56. A package according to claim 55 wherein the absorption enhancing substance is hydroxylamine or a non-toxic salt thereof.

57. A package according to claim 56 wherein the absorption enhancing substance is hydroxylamine hydrochloride.

58. A package according to claim 55 wherein (1) and (2) are kept separate prior to use.

59. A package according to claim 58 wherein (2) is hydroxylamine or a non-toxic salt thereof.

60. A package according to claim 59 wherein the absorption enhancing agent is hydroxylamine hydrochloride.

61. A package according to claim 55 wherein (1) is allopurinol.

62. A package according to claim 61 wherein the absorption enhancing substance is hydroxylamine or a non-toxic salt thereof.

63. A package according to claim 62 wherein the absorption enhancing substance is hydroxylamine hydrochloride.

64. A package according to claim 55 wherein (1) is alloxanthine.

65. A package according to claim 64 wherein the absorption enhancing substance is hydroxylamine or a non-toxic salt thereof.

66. A method of inhibiting xanthine oxidase during reperfusion, comprising intramuscularly administering to a mammal an xanthine oxidase inhibitor which is allopurine or alloxanthine in an amount sufficient to inhibit xanthine oxidase.

67. A method according to claim 66 wherein the mammal is human.

* * * * *

UNITED STATES PATENT AND TRADEMARK OFFICE
CERTIFICATE OF CORRECTION

PATENT NO. : 4,656,034
DATED : April 9, 1987
INVENTOR(S) : Stanley J. Sarnoff

It is certified that error appears in the above-identified patent and that said Letters Patent is hereby corrected as shown below:

Claim 16, line 5, delete "presenting" and insert --preventing--.

Signed and Sealed this

Thirteenth Day of March, 1990

*Attest:*

JEFFREY M. SAMUELS

*Attesting Officer*     *Acting Commissioner of Patents and Trademarks*